United States Patent
Sankaranarayanan

(10) Patent No.: US 6,248,895 B1
(45) Date of Patent: Jun. 19, 2001

(54) BENZOFUROXAN COMPOUND, METHOD OF PREPARATION, PHARMACEUTICAL COMPOSITION AND METHOD OF TREATMENT USING THE SAME

(75) Inventor: Alangudi Sankaranarayanan, Ahmedabad (IN)

(73) Assignee: Torrent Pharmaceuticals Ltd., Gujarat (IN)

( * ) Notice: Subject to any disclaimer, the term of this patent is extended or adjusted under 35 U.S.C. 154(b) by 0 days.

(21) Appl. No.: 09/565,917

(22) Filed: May 5, 2000

Related U.S. Application Data

(63) Continuation of application No. PCT/IB99/00892, filed on May 17, 1999.

(30) Foreign Application Priority Data

May 22, 1998 (IN) .......................................... 935/98

(51) Int. Cl.⁷ ...................... C07D 271/12; C07D 413/12; A61K 31/4245
(52) U.S. Cl. ........................................... 548/126; 514/361
(58) Field of Search .............................. 548/126; 514/361

(56) References Cited

U.S. PATENT DOCUMENTS 3,567,728 * 3/1971 Johnson et al. .................. 548/126 X (List continued on next page.)

FOREIGN PATENT DOCUMENTS 574 726 A1    12/1993  (EP).

(List continued on next page.)

OTHER PUBLICATIONS

Armstrong, P.W. and Moffat J.A., American J Medicine 1983; 27:74 (Suppl. 6B) :73.

(List continued on next page.)

*Primary Examiner*—Floyd D. Higel
(74) *Attorney, Agent, or Firm*—Sughrue, Mion, Zinn, Macpeak & Seas, PLLC

(57) ABSTRACT

The invention discloses a novel compound of the benzofuroxan series used for cardiovascular disorders represented by the general formula (I)

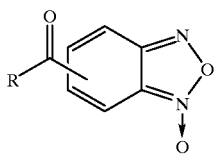

(I)

and pharmaceutically acceptable salts thereof wherein:

R is —O—(CH$_2$)n-X-R';
n=1 to 6;
X is —NHC(O)—, or oxygen;

R' is lower alkyl (C$_1$–C$_8$), aromatic, heteroaromatic, substituted or unsubstituted saturated heterocyclic ring with one or two hetero atoms such as nitrogen or oxygen wherein substitution is with lower alkyl; or R is selected from

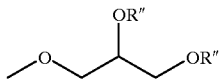 (a)

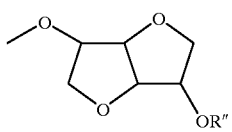

(b)

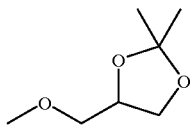

(c)

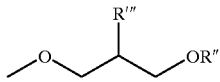

(d)

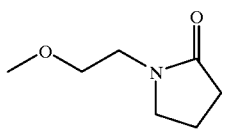

(e)

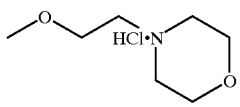

(f)

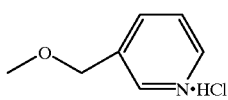

(g)

wherein R" is hydrogen, nitro, lower alkyl or —C(O)—R'" wherein R'" is hydrogen, lower alkyl or aryl.

The invention also discloses process for the preparation of compounds of general formula I.

The invention also discloses the use of the compounds of general formula I as defined above, as NO donors and/or in coronary heart diseases, and pharmaceutical compositions containing compounds of general formula I as active ingredients.

The invention also discloses a method of treatment of mammal, including man, of coronary heart disease by administration of an effective amount of a compound of formula I as defined above.

19 Claims, 2 Drawing Sheets

U.S. PATENT DOCUMENTS

| | | | | |
|---|---|---|---|---|
| 4,014,893 | * | 3/1977 | Crosby et al. | 548/126 |
| 4,185,018 | * | 1/1980 | Fah | 548/126 |
| 4,544,400 | * | 10/1985 | Anperson et al. | 548/126 X |
| 4,769,467 | * | 9/1988 | Imai | 548/126 |
| 5,032,604 | * | 7/1991 | Baldwin et al. | 514/361 |
| 5,272,164 | | 12/1993 | Izawa et al. | 514/357 |
| 5,424,326 | | 6/1995 | Schonafinger et al. | 514/364 |

FOREIGN PATENT DOCUMENTS

| | | | | |
|---|---|---|---|---|
| 2 029 412 | | 3/1980 | (GB) . | |
| 63-83078 | * | 4/1988 | (JP) | 548/126 |

OTHER PUBLICATIONS

Bassenge, E, et. al. Prog. Cardiovasc. Dis. 1988; 30:349–380.

Benedini, F. et. al. Journal of Medicinal Chemistry 1995; 38:130–136.

Boulton, A. J. et. al. Journal Chemical Society (C) 1966; 971–976 1966.

Boulton, A. J. et. al. Journal Chemical Society (B) 1967; 914–19.

Frampton, J. et. al. Drugs 1992; 44(4) 625–55.

Furchgott, R. F., et. al. nature 1980; 288:373–76.

Gasco, A. et. al. Liebigs Ann. chem. 1973; 10:587–90.

Ghosh, P. B. et. al. Journal of Medicinal Chemistry 1974; 17(2) :203–206.

Ghosh, P. B. et. al. Journal of Medicinal Chemistry 1972; 15(3) :255–260.

Ghosh, P. B. et. al. Journal of Medicinal Chemistry 1968; 11:305–311.

Ignarro, L.J. Circulation Res. 1989; 65:1–21.

Murad, F. Journal Clin. Invest. 1986; 78–1–5.

Nishikawa et al. Journal Pharmacol Exp. Ther. 1982; 220:183–190.

Needleman, P. et al. Journal Pharmacol Exp. Ther. 1973; 184:709–715.

Vanhoutte, P. M. Hypertension, 1989; 13:658–67.

Vane, J. R. et. al. The New England Journal of Medicine 1990: 323:27–36.

The Merck Manual of Diagnosis and Therapy (16th Edition 1992) pp. 498–505.

Martindale The Extra Pharmacopoeia (30th Edition 1993) pp. 1019–1026.

The Essential Guide to Prescription Drugs 1994 edited by James W Long and James J Raybacki pp. 42–46.

Harrison's Principles of Internal Medicine (13th Edition, 1994) pp. 1077–1084.

Goodman and Gilman's The Pharmacological Basis of Therapeutics (9th Edition 1996) pp. 759–767.

Katrnizky A.R. et al Journal of the Chemical Society, Perkin Transactions II, 1972, pp. 1682–1685.

* cited by examiner

BENZOFUROXAN COMPOUND, METHOD OF PREPARATION, PHARMACEUTICAL COMPOSITION AND METHOD OF TREATMENT USING THE SAME

This is a continuation application of international application No. PCT/IB99/00892 filed on May 17, 1999

BACKGROUND OF THE INVENTION

1. Field of the Invention

This invention relates to novel compounds of benzofuroxan series and to their use in therapeutics. In particular the invention concerns novel benzofuroxan derivatives, method for their preparation, pharmaceutical compositions containing these compounds, their use as tolerance resistant nitric oxide donors in treatment of angina pectoris.

2. Description of the Prior Art

After the discovery of endothelium-derived relaxing factor (EDRF) by Furchgott et al (1980), and the elucidation of the biochemistry of EDRF by a number of laboratories (Ignarro, 1989; Vane et al, 1990; Bassenge et al, 1988; and Vanhoutte, 1989), it is now widely accepted that EDRF is the endogenous nitrovasodilator, nitric oxide (NO) donor. The organic nitrates and related compounds owe their pharmacological action to the release of nitric oxide (NO) and these compounds are collectively called nitrovasodilators. NO stimulates the guanylate cyclase enzyme in vascular smooth muscle cells resulting in increased levels of cyclic GMP. This leads to dephosphorylation of myosin light chain which results in relaxation of smooth muscles (Murad, 1986). NO is known to be involved in a number of bio-regulatory processes like, vasodilatation, platelet deaggregation, vascular smooth muscle proliferation, etc. Organic nitrates are used in prophylaxis, treatment and management of patients with angina pectoris. These are also useful in congestive heart failure associated with acute myocardial infarction, hypertension associated with surgical procedures and to produce controlled hypotension during surgical procedures. Among organic nitrates, nitroglycerine (sublingual) which is currently in use, is the drug of choice for immediate relief of anginal symptoms. Prophylactic treatment of stable angina pectoris involves the use of one or more drugs such as long acting nitrates like isosorbide dinitrate, a beta-blocker and/or a calcium channel antagonist, particularly in patients likely to experience coronary spasm. In some cases this triple therapy satisfactorily control angina. They are quite effective in the treatment of these conditions when used intermittently.

Frequently repeated use of nitrates result in decrease in their pharmacological effects, a phenomenon well recognized as nitrate tolerance. The mechanism of tolerance is not well defined. As early as 1973, Needleman and Johnson (1973) have reported that tolerance to nitroglycerine could occur in isolated rabbit arteries. It was hypothesized by them that depletion of sulphydryl groups was associated with the development of tolerance to nitroglycerine. This is a major problem in the clinical use of organic nitrates (Frampton et al, 1992). Currently, the development of tolerance is reduced by the use of intermittent dosing schedule with a nitrate-free interval of 10–12 hrs. However, this intermittent use is associated with decreased exercise tolerance during the last part of nitrate-free interval. This suggests possibility of increased frequency of or severity of angina during nitrate-free interval. The importance of development of tolerance has increased as these drugs are used more commonly in various dosage forms like oral, transdermal, and intravenous preparations and even as sustained-release preparations. Several indirect indices like exercise duration, systemic blood pressure, pulmonary artery pressures and pulmonary artery wedge pressure has been used to assess tolerance to organic nitrates. However, it is not clear whether decreased response to nitrates is due to tolerance of the vascular smooth muscle cells or changes in regulatory factors like activation of neurohumoral factors or fluid retention etc. (Armstrong and Moffat, 1983). Irrespective of the mechanisms of tolerance development, clinically it is important to develop nitric oxide donors with least tendency to develop tolerance.

P B Ghosh et al. (Journal of Medicinal Chemistry, 1968) disclosed the method of synthesis of various benzo-2,1,3-oxadiazoles (benzofurazans) and their N-oxides (benzofuroxans) and their potential as antileukemic and immuno-suppressive drugs in vitro.

P B Ghosh et al. (Journal of Medicinal Chemistry, 1972) tested 4-nitro benzofurazans and 4-nitrobenzofuroxans bearing electron withdrawing substitutents in the 5 and 6 position (relative to $NO_2$) as potential antileukemic and immuno suppressive drugs in vitro.

Nishikawa et al. (The Journal of Pharmacology and Experimental Therapeutics, 1982) disclosed effect of N-ethoxycarbonyl-3-morpholinosydnonimine and its metabolites 3-morpholinosydnonimine, cyanomethyleneamino morpholine, N-nitroso-N-morpholinoamino acetonitrile as novel antianginal agents.

F. Murad (J. Clin. Invest, 1986) disclosed cyclic guanosine monophosphate as a mediator of vasodilation.

James Frampton et al. (Drug Evaluation, Adis International Limited, 1992) gives a review of pharmacology and therapeutic efficiency of nicorandil in angina pectoris. Nicorandil, which has both vasodilator and venodilating properties was found to offer an effective alternative to established vasodilator therapy with conventional nitrates and calcium antagonists in the long term treatment of stable angina pectoris.

U.S. Pat. No. 5,272,164 disclosed novel carboximidamide derivatives particularly N-cyano-$N^1$-substituted pyridine carboximidamide derivatives having vasodilating effect and hypotensive effect besides other physiological effects which are helpful in treatment of ischemic heart diseases.

U.S. Pat. No. 5,424,326 disclosed phenyl-1,2,5-oxadiazole carboxamide-2-oxide and its derivatives, which are useful for the treatment of disorders of the cardiovascular system.

F Benedini et. al. (J. Med. Chem. 1995) disclosed a new nitro ester-3-[(nitroxy) alkyl]-2H-1,3-benzoxazin-4(3H)-ones showing marked inhibitory activity against ischemia-induced electrocardiographic changes, with only limited systemic hemodynamic effects. These new nitro ester derivatives, endowed with marked anti-anginal activity, which is not associated with concurrent and pronounced fall in systemic blood pressure, are indicative of a new class of selective nitrovasodilators having a preferential action on large coronary vessels, which could be clinically relevant in the treatment of coronary artery diseases.

However, none of the above prior art disclosures on the drugs specifically used as vasodilator for treatment of cardiac ailments tackles the problem associated with the conventional NO-donors to develop tolerance in the patient after continuous use for a period of time. The present invention evaluates the benzofuroxan derivatives for their NO donor activities particularly with reference to their tendency to develop tolerance for continued application of the drug. Significantly, the invention identifies the molecules showing vasodilator activity without tendency to develop tolerance unlike the conventional nitric-oxide donors.

SUMMARY OF THE INVENTION

The present invention provides, in the first aspect, novel benzofuroxan derivatives and pharmaceutically acceptable salts thereof Such salts include, but are not limited to, oxalate, tartarate, maleate, methyl sulphonate, p-toluene sulphonate etc.

The invention further provides the use of the benzofuroxan derivatives as tolerance resistant nitric oxide donors.

The invention further provides pharmaceutical formulations comprising benzofuroxan derivatives to be used as tolerance resistant nitric oxide donors.

The invention in a further aspect, provides the process of preparation of the novel benzofuroxan derivatives.

The invention also provides for a method of treatment of mammals including man of coronary heart diseases by administration of a compound of benzofuroxan series.

DETAILED DESCRIPTION OF THE INVENTION

Figure 1:
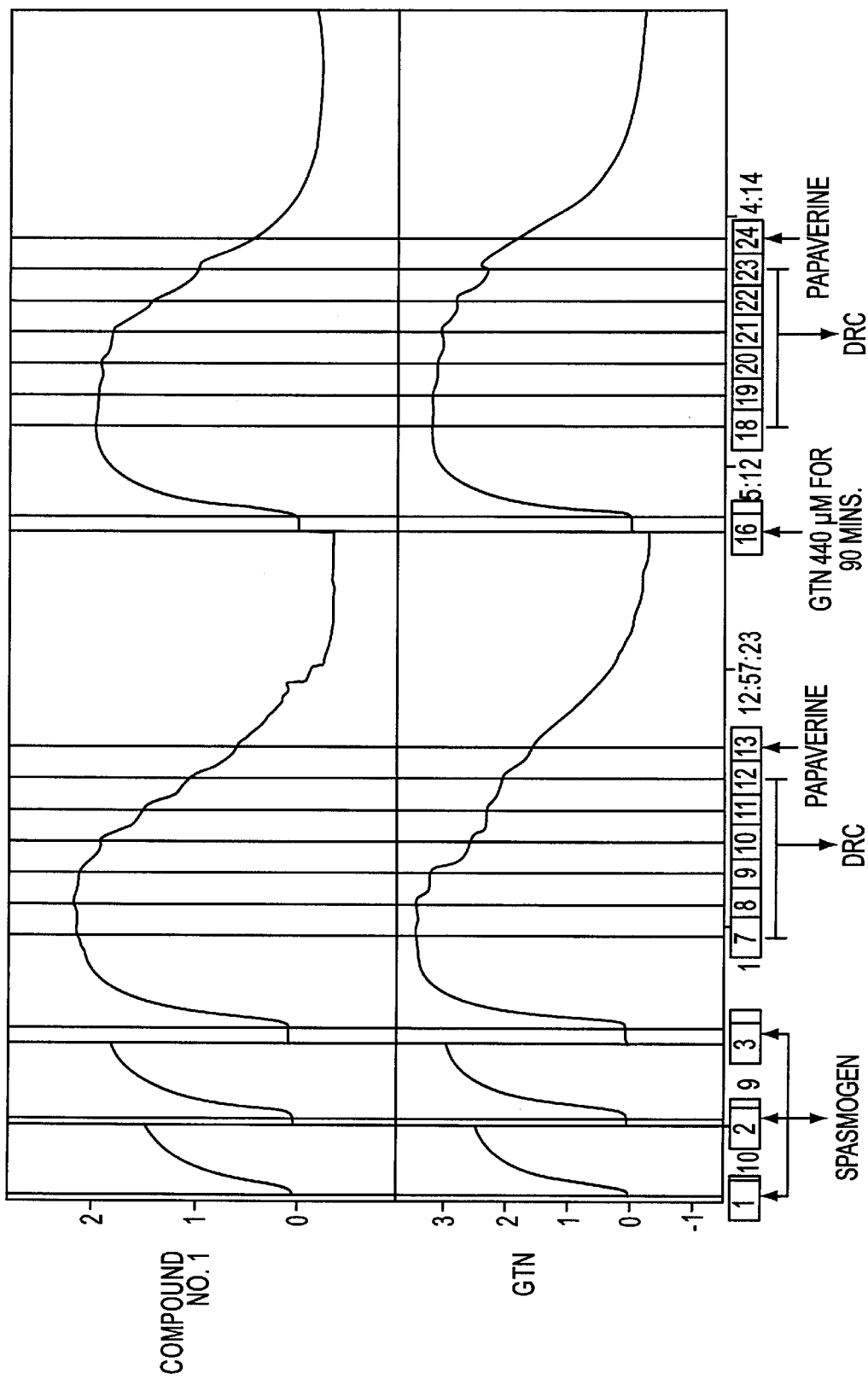
FIG. 1 gives the dose response curve for the test compound (compound No. 1) and GTN.

The novel compounds of the benzofuroxan series used for cardiovascular disorders are represented by the general formula (I).

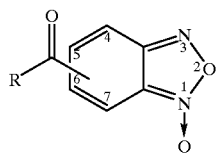
(I)

and pharmaceutically acceptable salts thereof
wherein:
R is —O—(CH$_2$)$_n$-X-R';
n=1 to 6;
X is —NHC(O)— or oxygen;
R' is lower alkyl (C$_1$–C$_8$), aromatic, heteroaromatic, substituted or unsubstituted saturated heterocyclic ring with one or two hetero atoms such as nitrogen or oxygen wherein substitution is with lower alkyl, or R is selected from

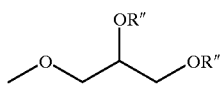
(a)

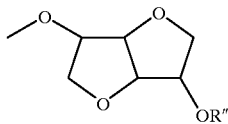
(b)

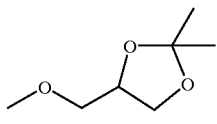
(c)

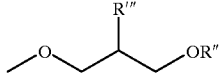
(d)

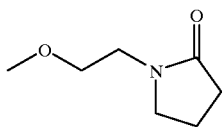
(e)

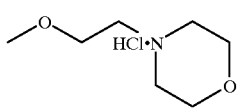
(f)

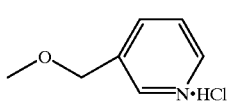
(g)

wherein R" is hydrogen, nitro, lower alkyl or —C(O)—R'"

wherein R'" is hydrogen, lower alkyl or aryl

The representative compounds of the invention showing tolerance resistant NO donor activities as defined above are given in the Table-1.

TABLE 1

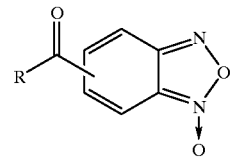
(I)

| Compound No. | R |
|---|---|
| 1 | —OCH$_2$CH$_2$—NHCO-3-pyridyl.HCl |
| 2 | —OCH$_2$CH$_2$—NHCO-4-pyridyl.HCl |
| 3 | substitution (e) |
| 4 | substitution (h) |
| 5 | —OCH$_2$CH$_2$—N-morpholinyl.HCl (substitution f) |
| 6 | —OCH$_2$CH$_2$OMe |
| 7 | substitution (i) |
| 8 | —OCH$_2$CH$_2$O—CH$_2$CH$_3$ |
| 9 | —OCH$_2$-3-pyridyl.HCl (substitution g) |
| 10 | substitution (c) |
| 11 | substitution (j) |

TABLE 1-continued (Structure I: benzofuroxan with R-C(=O)- substituent)

| Compound No. | R |
|---|---|
| (h) | -O-CH2-CH(CH3)-OH (2-hydroxypropyloxy group) |
| (i) | -O-CH2-CH(OH)-CH2-OH (2,3-dihydroxypropyloxy group) |
| (j) | isosorbide-NO2 group |

The present invention also provides a process for the preparation of novel benzofuroxan derivatives of the general formula (I), and their pharmaceutically acceptable salts, wherein one of the processes comprises, (a) reacting chloro carbonyl benzofuroxan and an alcohol in solvent such as. tetrahydrofuran at room temperature;
(b) adding a base such as triethylamine to the reaction mixture;
(c) refluxing the reaction mixture till the completion of the reaction;
(d) removal of the solvent followed by addition of water and extraction with organic solvent such as ethyl acetate;
(e) concentration of ethyl acetate layer;
(f) purification by column chromatography; and
(g) optionally transforming into the corresponding pharmaceutically acceptable salts Said products of steps (f) and (g) are characterized by m.p. and the conventional spectroscopic techniques.

The present invention also provides a process for the preparation of novel benzofuroxan derivatives of the general formula (I), and their pharmaceutically acceptable salts, wherein the said process comprises, (a) reacting carboxy benzofuroxan with saturated solution of alcoholic HCl;
(b) removal of excess of alcohol under reduced pressure to get the residue;
(c) purification by column chromatography; and
(d) optionally transforming into the corresponding pharmaceutically acceptable salts.

Said products of steps (c) and (d) are characterized by m.p. and the conventional spectroscopic techniques.

Such products can also be prepared by the other equivalent processes of ester formation, which comprises, (a) reacting carboxy benzofuroxan and an equimolar amount of an alcohol such as N-(2-hydroxyethyl)-nicotinamide, N-(2-hydroxyethyl) isonicotinamide, N-(2-hydroxyethyl)-2-pyrolidinone, N-(2-hydroxyethyl) morpholine, propylene glycol, methylcellosolve, ethylcellosolve, pyridine -3-methanol, solketal, isosorbide -5-mononitrate, etc. in methylene chloride;
(b) adding 4-dimethylamino pyridine and N,N'-dicyclohexyl carbodiimide under stirring and continuing the stirring for a period of 2 to 16 hours at room temperature to complete the reaction;
(c) filtering the reaction mixture when the filtrate on evaporation under reduced pressure gives the crude product;
(d) purifying the product thus obtained by column chromatography; and
(e) optionally transforming into the corresponding pharmaceutically acceptable salts.

The said product of steps (d) and (e) are characterized by m.p. and the conventional spectroscopic techniques.

The invention also provides a process for the preparation of 5(6)-[(2,3-dihydroxy propyloxy) carbonyl] benzofuroxan, (Compound 7), wherein said process comprises, (a) reacting a mixture of 5(6)-((±)-2,2-dimethyl-1,3-dioxolane-4-methyloxy carbonyl) benzofuroxan and acid such as 75% acetic acid and stirring at 80° C. for 4 hours;
(b) evaporating the solvent under vacuum to give an oily product; and
(c) purifying the product of step (b) by column chromatography.

Said product of step (c) is characterized by m.p and the conventional spectroscopic techniques.

Pharmaceutical Compositions for No-Donor Molecules

The compounds according to this invention as given by general formula (I) or their salts or complexes can be administered orally, intravenously or parenterally as a pharmaceutical preparation in liquid or solid form. It may also be administered via topical, transdermal, sublingual, buccal or rectal route for example as a suppository, ointment, cream, powder, transdermal patch, metered aerosol or spray.

The pharmaceutically acceptable carriers present in the composition of this invention are materials recommended for the purpose of administering the medicament. These may be liquid or solid materials, which are otherwise inert or medically acceptable and are compatible with the active ingredients.

Evaluation of the Biological Activity

Methods a) In vitro Screening of NO Donors

The method adopted was a modified method of Nishikawa et al (1982). Albino rabbits of either sex were stunned and exsanguinated. Thoracic aorta was quickly removed and cut helically (at an angle of 450) into strips 4–5 mm wide and 25 to 30 mm long, after removal of adventitial connective tissue. The endothelium was rubbed off gently using a cotton swab soaked in Kreb's solution. Two strips were fixed vertically in organ baths containing 20 ml. Kreb's solution maintained at 37° C. and bubbled with oxygen. A resting tension of 4 g was applied and the preparation was allowed to equilibrate for 30 min. Each preparation was exposed to two primer doses of KCl (30 mM). After the contraction reached a maximum, the bath was drained off and replaced with fresh Kreb's solution. Half an hour later, cumulative dose response curve for the test compound was taken on one tissue (test) and for glyceryl trinitrate (GTN) in the other (standard). The dose range used was from $10^{-9}$ M to $10^{-3}$ M with a contact period of 4 min. for each dose. After the maximum relaxation was achieved with the last dose, papaverine ($10^{-4}$ M) was added to obtain the maximum relaxation.

Tolerance was induced in both the tissues by adding 440 µM of GTN for 90 minutes. During this period the bath solution was changed every 30 min. and 440 µM of GTN was replaced. Later both the tissues were washed thoroughly and the dose response curve (DRC) for both the test and the standard were repeated. The percentage relaxation with individual doses was calculated by taking the maximum relaxations to $10^{-4}$ M papaverine as 100% relaxation. A graph was plotted by taking the percentage relaxation vs the log (M) concentration of the compounds. The relaxant activity of the test compound was assessed by calculating the mean relative potencies (MRP) and the mean activity ratio (MAR), both before and after tolerance, as defined below:

$$MPR = \frac{\text{Concentration of } GTN \text{ producing } 50\% \text{ of its maximum relaxation}}{\text{Concentration of test compound producing } 50\% \text{ of the maximum relaxation of } GTN.}$$

$$MAR = \frac{\text{Maximum relaxation produced by the test compound}}{\text{Maximum relaxation produced by } GTN}$$

Figure 2:
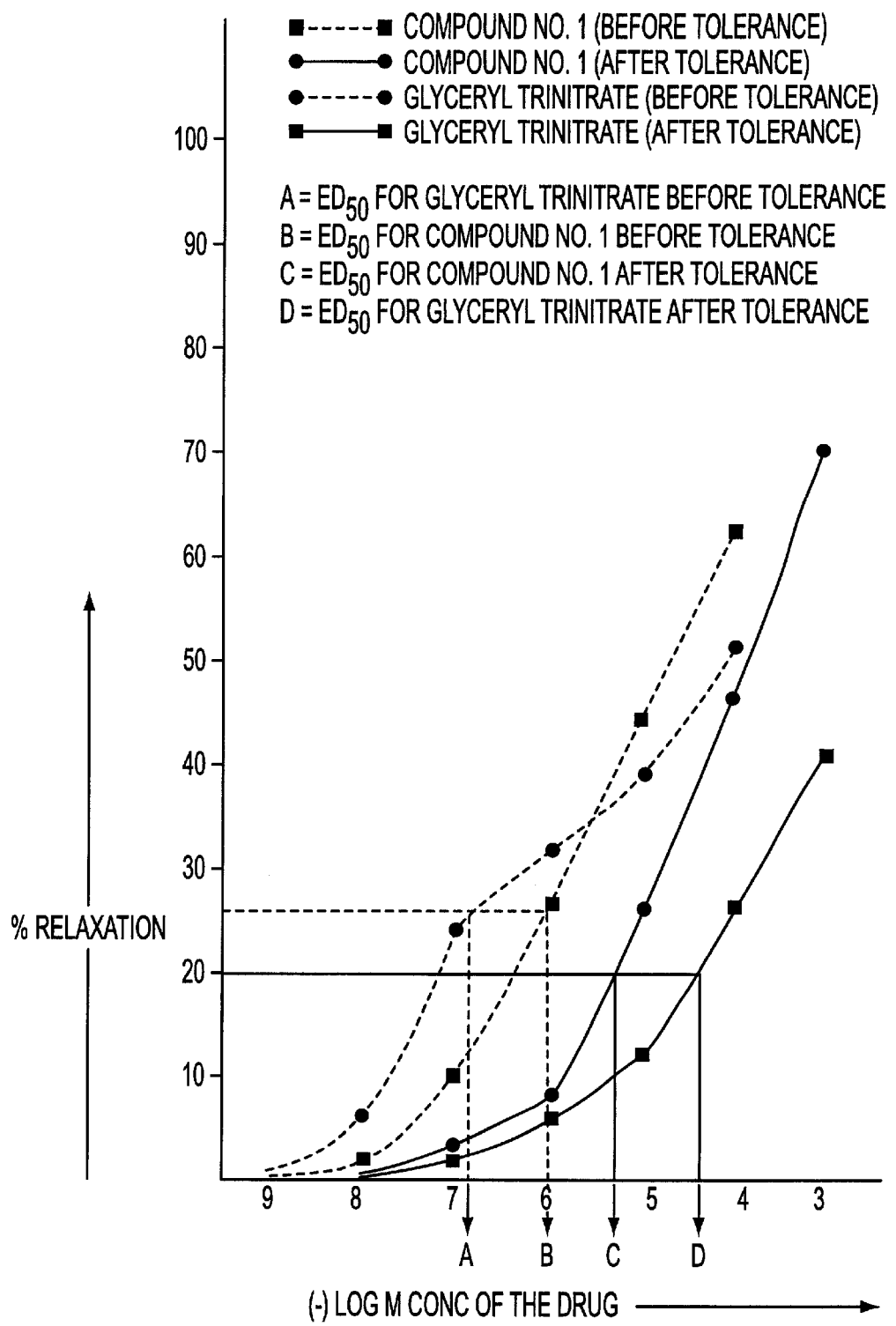
FIG. 2 gives the dose response curves (percentage relaxation vs the log(M) concentration) for GTN and a test compound No. 1 before and after development of tolerance.

Selection criteria for in vivo study: Compounds having MRP greater than 3 and MAR greater than 1.3 after tolerance were selected for in vivo study. Dose response curve for compound 1 is given in FIGS. 1 and 2 of the accompanying drawings as an example for the estimation of MRP and MAR.

b) In vivo Pharmacological Screening

A modified method of Benedini et al (1995) was adopted for studying the anti-anginal effect of the chosen compounds. Guinea pigs of either sex, weighing approximately 400–600 g were used for this study. Animals were anesthetized with urethane (1.25 g/kg, i.p.) and jugular vein was cannulated for intravenous administration of drugs/vehicle. Mean arterial blood pressure (MABP) was monitored by a cannula inserted into the right carotid artery and connected to a pressure transducer. Standard limb lead II electrocardiogram was recorded continuously. All the recordings were carried out on a MacLab system (AD Instruments, UK).

The ability of the test compounds to suppress the vasopressin induced T-wave elevation was used as the model for studying the anti-anginal effects of the compounds. Guinea pigs were divided into two groups for the purpose of this study, i) control group (pretreated with the vehicle for the compound) and ii) drug treated group.

i) Control Group

In this group of animals the solvent used for dissolving the test compound was administered intravenously in a volume of 1 ml/kg. The basal T-wave heights, heart rates and MABP and changes after vehicle administration were noted. Thirty seconds later 1 I.U./ml/kg of vasopressin was administered intravenously. The T-wave heights, heart rates and MABP and their changes after vasopressin administration were also noted. The T-wave elevation (after vasopressin administration), maximum rise in MABP, and changes in heart rate were calculated from the above data and expressed as mean±standard deviation.

ii) Drug Treated Group

The effects of the test compound in suppressing the T-wave elevation caused by vasopressin were evaluated with atleast three dose levels. Groups of 6 guinea pigs were used for each dose. The test compound was injected 30 seconds prior to vasopressin administration. Changes in MABP, heart rate and T-waves were recorded as described for the control group. The percentage inhibition of vasopressin induced T-wave elevation was calculated for each dose taking the T-wave height estimated in control group as 100%. From the dose vs percent inhibition relationship, the dose required for 50% inhibition ($ED_{50}$) for the T-wave elevation was estimated.

Determination of the $Ed_{20}$ Values for Drop in Mabp

In a separate group of animals the drop in MABP after administration of the test compound (dose range of 0.1–1000 µg/kg, i.v.) was studied. Atleast three animals were used for each dose. Care was taken so that the doses were given only after the MABP had stabilized from the effects of the previous dose. All doses were injected in a final volume of 1 ml/kg. The drop in MABP was noted for increasing concentrations of the test compound and a dose response curve was drawn. From this graph the dose required to produce a 20% fall in MABP ($ED_{20}$) was calculated. The specificity of the test compound was defined by the selectivity index, which was shown below:

$$\text{Selectivity Index} = \frac{\text{Dose required for 20\% reduction in } MABP\ (\mu g/kg)}{\text{Dose required for 50\% inhibition of } T\text{-wave elevation } (\mu g/kg.)}$$

Compounds having selectivity ratio greater than 30 times that of GTN were selected toxicology evaluation. The selectivity index for GTN was estimated to be 0.017.

Results of in vitro Screening of NO Donors

The results of in vitro screening of the NO donors are given in the following Table 2.

TABLE 2

In vitro activity of NO donors

| Compound No | Mean Relative Potency | | Mean Activity Ratio | |
|---|---|---|---|---|
| | Before Tolerance | After Tolerance | Before Tolerance | After Tolerance |
| 1 | 0.2 | 8.4 | 1.3 | 1.7 |
| 2 | 0.06 | 6.94 | 1.19 | 2.38 |
| 3 | 0.11 | 25 | 1.15 | 1.83 |
| 4 | 0.28 | 11.22 | 1.13 | 1.69 |
| 5 | 0.18 | 4.12 | 1.08 | 1.22 |
| 6 | 0.97 | 17.02 | 1.74 | 2.32 |
| 7 | 0.17 | 3.49 | 1.16 | 1.58 |
| 8 | 0.2 | 11.9 | 1.04 | 1.97 |
| 9 | 0.53 | 8.05 | 1.23 | 1.7 |
| 10 | 0.39 | 10.13 | 1.05 | 1.57 |
| 11 | 0.25 | 7 | 1.37 | 1.63 |

Results of in vivo Evaluation

The compounds, which were selected based on in-vitro studies, were subjected to in-vivo studies to assess their anti-anginal action. Compounds with sufficient selectivity (i.e. lower hypotension) and anti-anginal action are listed in Table -3.

TABLE 3

In vivo activity of selected Nitric Oxide donors

| Compound | Dose needed for 20% fall in B.P. ($ED_{20}$ µg/kg, i.v.) (A) | Dose required for 50% inhibition of T-wave ($ED_{50}$ µg/kg, i.v.) (B) | Selectivity Index A/B (C) |
|---|---|---|---|
| GTN | 8.22 | 474.40 | 0.017 |
| 1 | 458.02 | 886.42 | 0.517 |
| 3 | 139.52 | 675.61 | 0.152 |

TABLE 3-continued

In vivo activity of selected Nitric Oxide donors

| Compound | Dose needed for 20% fall in B.P. (ED$_{20}$ μg/kg, i.v.) (A) | Dose required for 50% inhibition of T-wave (ED$_{50}$ μg/kg, i.v.) (B) | Selectivity Index A/B (C) |
|---|---|---|---|
| 6 | 226.34 | 337.90 | 0.67 |
| 9 | 227.16 | 372.85 | 0.61 |
| 10 | 286.00 | 492.00 | 0.58 |

It was observed that compounds 1, 6, 9 and 10 have a high selectivity index as compared to GTN. In the case of these compounds, the index is significantly higher. The index showed that these compounds could elicit anti-anginal activity at a dose, which had minimum systemic effects. Their selectivity in dilating the coronary arteries was quite high as compared to a conventional drug like GTN.

The high selectivity index of these compounds as compared to nitroglycerine show that they selectively dilate the coronary arteries and have a lower tendency to cause hypotension during clinical usage. For example, compound 1 is 30 times more selective as compared to GTN. This shows that these compounds have very little tendency to cause hypotension. Conventional nitrates like GTN cause tachycardia, retrosternal discomfort, palpitations, collapse, syncope and postural hypotension, etc as a manifestation of hypotensive effect. This could limit their use in selected patients. However, the compounds described in this invention due to a lower tendency to cause hypotension are superior to conventional nitrates.

The benzofuroxans described in this invention can be used in cardiovascular disorders like acute effort angina, angina prophylaxis, mixed angina and silent ischemia, acute myocardial infarction, congestive heart failure, etc. They can be used alone or in combination with beta adrenergic blockers like propranolol, atenolol, carvedilol, etc. and calcium channel antagonists like verapamil, diltiazem, etc.

The following examples are presented to further illustrate the invention but do not limit it in any way.
The method of preparation of the novel compounds of this invention are given in the following examples:

EXAMPLE 1
Preparation of 5(6)-(2-nicotinamide ethyloxycarbonyl) benzofuroxan hydrochloride (Compound 1)

In 20 ml of methylene chloride, 0.9 g of 5(6)-carboxy benzofuroxan was added at room temperature. To this solution was added 0.83 g of N-2-hydroxyethyl nicotinamide. Then 1.1 g of dicyclohexyl carbodiimide and 4-dimethylaminopyridine (70 mg) were added at room temperature and the reaction mixture was stirred at room temperature for 16 hours. Methylene chloride was removed on a rotary evaporator under reduced pressure to give a gummy material which was purified by column chromatography using hexane:ethyl acetate (5:7) to give 300 mg of solid.

100 mg of the above solid was dissolved in 10 ml of methanol at 0° C. To it was added 5 ml of methanolic HCl solution and the reaction mixture was warmed to room temperature and stirred for 15 minutes to give 90 mg of 5(6)-(2-nicotinamide ethyloxycarbonyl) benzofuroxan hydrochloride.

m. p.: 202–205° C.

IR(KBr): 1711, 1666, 1607, 1576, 1547, 1020 cm$^{-1}$

PMR (CDCl$_3$, 300 MHz) δ: 8.99 (1H,s), 8.75 (1H,s), 8.23 (1H,s), 8.13 (1H,d,J=9 Hz), 7.85 (1H,s), 7.4 (2H,s), 6.85 (1H,s), 4.6 (2H,s), 3.92 (2H,s)

Alternatively, compound 1 can also be prepared by following procedure.

5(6)-Chlorocarbonyl benzofuroxan (100 mg) and N-2-hydroxy ethyl nicotinamide (150 mg) were dissolved in THF (10 ml) at room temperature. To the reaction mixture triethylamine (0.1 ml) was added and reaction mixture was refluxed for 24 hrs. THF was removed under reduced pressure. To the residue 10 ml water was added and extracted with ethyl acetate (3×20 ml). Ethyl acetate was removed under reduced pressure to get sticky mass which was purified by column chromatography using EtOAc: n-hexane (90:10) to give 65 mg of compound 1.

EXAMPLE 2
Preparation of 5(6)-(2-isonicotinamideethyloxycarbonyl) benzofuroxan (Compound 2)

5(6)-Carboxy benzofuroxan (1.8 g, 0.01 mole) and N-(2-hydroxyethyl) isonicotinamide (1.66 g, 0.01 mole) were dissolved in CH$_2$Cl$_2$ (100 ml) and THF (100 ml) mixture. To this solution, 4-dimethylamino pyridine (70 mg) and N,N'-dicyclohexyl carbodiimide (3 g, 0.0145 mole) were added under stirring. The reaction mixture was stirred for 16 hours at room temperature. It was filtered and the filtrate on evaporation under reduced pressure gave crude product which was purified by column chromatography (EtOAc:n-hexane=90:10) to give the title compound as yellow solid (0.2 g, 74%).

m.p.: 201° C. (HCl salt)

IR(KBr): 3423, 3180, 1720, 1677, 1613, 1585, 1543, 1490 cm$^1$

PMR (200 MHz, CDCl$_3$) δ: 2.58–2.6 (2H,t,J=1.7 Hz), 3.55 (1H,s), 4.52–4.57 (2H,t,J=5.26 Hz), 7.67–8.45 (3H,m), 8.95–9.65 (4H,dd)

Mass: 328 (M$^+$)298, 229, 181, 164, 147, 117, 105, 77, 50.

EXAMPLE 3
Preparation of 5(6)-(2-pyrolidinone ethyloxy carbonyl) benzofuroxan (Compound 3)

5(6)-Carboxy benzofuroxan (0.9 g, 0.005 mole) and 1-(2-hydroxyethyl)-2-pyrolidinone (0.7 g, 0.005 mole) were dissolved in CH$_2$Cl$_2$ (40 ml). To this solution, 4-dimethyl amino pyridine (70 mg) and N,N'-dicyclohexyl carbodiimide (2.06 g, 0.01 mole) were added under stirring. The reaction mixture was stirred for 3 hours at room temperature. It was filtered and the filtrate on evaporation under reduced pressure gave crude product, which was purified by column chromatography (EtOAc:n-hexane=50:50) to give the title compound as pale yellow solid (0.7 g, 48%).

m.p.: 101–102° C.

IR (Br): 1726. 1678, 1611., 1590,. 1534 cm$^{-1}$

PMR (200 MHz, CDCl$_3$) δ: 1.99–2.14 (2H,m), 2.35–2.43 (2H,t,J=7.72 Hz), 3.49–3.56 (2H,t,J=6.9 Hz), 3.68–3.73 (2H,t,J=5.2 Hz), 4.48–4.53 (2H,t,J=5.4 Hz), 7.6–7.86 (3H, m)

Mass: 291 (M$^+$), 273, 225, 111, 98, 70, 56.

EXAMPLE 4
Preparation of 5(6)-(2-hydroxy propyloxy carbonyl) benzofuroxan (Compound 4)

5(6)-Carboxy benzofuroxan (1.8 g, 0.01 mole) and propylene glycol (0.76 g, 0.01 mole) were dissolved in CH$_2$Cl$_2$ (80 ml). To this solution, 4-dimethylamino pyridine (140 mg) and N,N'-dicyclohexyl carbodiimide (4.4 g, 0.021 mole) were added with stirring. The reaction mixture was stirred for 2 hours at room temperature. It was filtered and the filtrate on evaporation under reduced pressure gave crude product which was purified by column chromatography (EtOAc:n-hexane=20:80) to give the title product as pale yellow solid (1.16 g, 49%)

m.p.: 89–90° C.

IR(KBr): 3500–3100, 1716, 1654, 1613, 1592, 1540, 1491 cm$^{-1}$

PMR (200 MHz, CDCl$_3$) δ: 1.3–1.33 (3H,d,J=6 Hz), 3.82 (1H,s), 4.22–4.4 (3H,m), 7.6–8.26 (3H,m)

Mass: 238 (M$^+$), 179, 163, 147, 103, 75, 58, 45.

EXAMPLE 5

Preparation of 5(6)-(2-morpholino ethyloxy carbonyl) benzofuroxan (Compound 5)

5(6)-Carboxy benzofuroxan (0.9 g, 0.005 mole) and N-(2-hydroxyethyl) morpholine (0.71 g, 0.005 mole) were dissolved in CH$_2$Cl$_2$ (50 ml). To this solution, 4-dimethylamino pyridine (70 mg) and N, N'-dicyclohexyl carbodiimide (2.06 g, 0.01 mole) were added under stirring. The reaction mixture was stirred for 2 hours at room temperature. It was filtered and the filtrate on evaporation under reduced pressure gave crude product which was purified by column chromatography (EtOAc:n-hexane=50:50) to give the title compound 5 as white solid (0.5 g, 34%)

The base (0.2 g) was transformed into the corresponding HCl salt, by 5% methanolic HCl (0.14 g, 64%)

m.p.: 210° C. (HCl salt)

IR(KBr): 1729, 1613, 1589, 1542 cm$^{-1}$

PMR (200 MHz, CDCl$_3$) δ: 2.58–2.59 (4H,t,J=4.5 Hz), 3.18–3.2 (4H,t,J=13.63 Hz), 3.55–3.43 (2H,t), 3.97–4.17 (2H,t), 7.48–7.98 (3H,m)

Mass: 293 (M$^+$), 113, 103, 101, 100

EXAMPLE 6

Preparation of 5(6)-(2-methyloxy ethyloxy carbonyl) benzofuroxan (Compound 6)

5(6)-Carboxy benzofuroxan (1.8 g, 0.01 mole) and methyl cellosolve (0.076 g, 0.01 mole) were dissolved in CH$_2$Cl$_2$ (60 ml). To this solution, 4-dimethylamino pyridine (0.3 g) and N,N'-dicyclohexyl carbodiimide (2.3 g, 0.01 mole) were added with stirring. The reaction mixture was stirred for 2 hours at room temperature. It was filtered and the filtrate on evaporation under reduced pressure gave crude product as oily liquid. Crude product was purified by column chromatography (EtOAc:n-hexane=5:95) to give the title compound. It was crystallized from n-hexane to yield 5(6)-methyloxy ethyloxy carbonyl benzofuroxan as yellow solid (1.2 g, 50%).

m.p.: 68–69° C.

IR(KBr): 1717, 1615, 1582, 1536 cm$^{-1}$

PMR (300 MHz, CDCl$_3$) δ: 3.43 (3H,s), 3.72–3.75 (2H,t,J=6 Hz), 4.5–4.53 (2H,t,J=6 Hz), 7.26–8.26 (3H,m).

Mass: 238 (M$^+$), 207, 180, 163, 103, 75, 58.

Alternatively, compound 6 can also be prepared by following procedure:

5(6)-Carboxy benzofuroxan (1.0 g) was heated to 80° C. in a saturated solution of methyl cellosolve HCl for 16 hours. Excess methyl cellosolve was removed under vacuum and the residue was redissolved in diethylether and washed with aqueous NaOH, followed by water and dried over Na$_2$SO$_4$. Ether was removed under vacuum and the residue was purified by column chromatography to get 280 mg. of compound 6.

EXAMPLE 7

Preparation of 5(6)-(2,3-dihydroxy propyloxy carbonyl) benzofuroxan (Compound 7)

A mixture of 5(6)-((±)-2,2-dimethyl-1,3-dioxolane-4-methyloxy carbonyl) benzofuroxan (0.5 g, 0.001 mole) and 5 ml of 75% acetic acid was stirred at 80° C. for 4 hours. Evaporation of the solvent under vacuum (40° C.) gave oily product, which was purified by column chromatography (hexane:EtOAc=80:20) to give the title compound as yellow solid (0.4 g, 93%)

m.p.: 86° C.

IR (KBr): 3355, 1719, 1606, 1450 cm$^{-1}$

PMR (300 MHz, CDCl$_3$) δ: 3.89–3.90 (1H,d,J=4.2 Hz), 4.03–4.06 (1H,t,J=4.5 Hz), 4.36–4.52 (2H,m), 7.61–8.34 (3H,m)

Mass: 254 (M$^+$), 180, 163, 103

EXAMPLE 8

Preparation of 5(6)-(2-ethoxy ethyloxy carbonyl) benzofuroxan (Compound 8)

5(6)-Carboxy benzofuroxan (1.8 g, 0.01 mole) and ethylcellosolve (0.8 g, 0.01 mole) were dissolved in CH$_2$Cl$_2$ (50 ml). To this solution, 4-dimethylamino pyridine (0.3 g) and N,N'-dicyclohexyl carbodiimide (2.4 g, 0.011 mole) were added under stirring. The reaction mixture was stirred for 2 hours at room temperature. It was filtered and the filtrate on evaporation under reduced pressure gave crude product as brown oily liquid, which was purified by column chromatography (EtOAc:n-hexane=20:80) to yield the title compound as pale yellow viscous oil (1.0 g, 40%)

IR(KBr): 1727, 1598, 1538, 1488 cm$^{-1}$

PMR (200 MHz, CDCl$_3$) δ: 1.2–1.27 (3H,t,J=7 Hz), 3.54–3.64 (2H,q,J=7 Hz), 3.76–3.81 (2H,t,J=6 Hz), 4.5–4.54 (2H,t,J=5 Hz), 7.59–8.26 (3H,m)

EXAMPLE 9

Preparation of 5(6)-(3-pyridine methoxy carbonyl) benzofuroxan (Compound 9)

5(6)-Carboxy benzofuroxan (1.8 g, 0.01 mole) and pyridine-3-methanol (1.1 g, 0.01 mole) were dissolved in CH$_2$Cl$_2$ (50 ml). To this solution, 4-dimethylamino pyridine (70 mg) and N,N'-dicyclohexyl carbodiimide (3 g, 0.014 mole) were added with stirring. The reaction mixture was stirred for 2 hours at room temperature. It was filtered and the filtrate on evaporation under reduced pressure gave crude product, which was purified by column chromatography (EtOAc:n-hexane=25:75) to give the title compound as a pale yellow solid. The base (0.5 g) was transformed into the corresponding HCl salt, by 5% methanolic HCl (0.4 g, 71%)

m.p.: 200° C. (HCl salt)

IR(KBr): 1719, 1616, 1589, 1534 cm$^{-1}$

PMR (300 MHz, DMSOd6) δ: 5.59 (2H,s), 7.88–8.04 (3H,m), 8.63–9.09 (4H,m)

Mass: 307 (M$^+$+HCl), 271 (M$^+$), 180, 92.

EXAMPLE 10

Preparation of 5(6)-((±)-2,2-dimethyl-1,3-dioxolane-4-methyloxy carbonyl) benzofuroxan (Compound 10)

5(6)-Carboxy benzofuroxan (0.99 g, 0.005 mole) and solketal (0.66 g, 0.005 mole) were dissolved in CH$_2$Cl$_2$ (40 ml). To this solution, 4-dimethylamino pyridine (0.2 g) and N,N'-dicyclohexyl carbodiimide (1.33 g, 0.006 mole) were added under stirring. The reaction mixture was stirred for 2 hours at room temperature. It was filtered and the filtrate on evaporation under reduced pressure gave crude product as oily liquid, which was purified by column chromatography (EtOAc:n-hexane=10:90) to give the title compound as pale yellow solid (0.6 g, 41%)

m.p.: 51–52° C.

IR (KBr): 1725, 1586, 1535, 1484 cm$^{-1}$

PMR (200 MHz, CDCl$_3$) δ: 1.39 (3H,s), 1.46 (3H,s), 3.83–3.89 (1H,dd,6 Hz), 4.13–4.20 (1H,dd,6 Hz), 4.39–4.48 (3H,m), 7.85–8.27 (3H,m)

Mass: 294 (M$^+$), 279, 163.

EXAMPLE 11

Preparation of 5(6)-(isosorbide mononitrateoxy carbonyl) benzofuroxan (Compound 11)

To a solution of 5(6)-carboxy benzofuroxan (1.0 g, 0.0055 mole) and isosorbide -5-mononitrate (0.09 g, 0.0047 mole) in $CH_2Cl_2$ (50 ml) were added 4-dimethylamino pyridine (50 mg) and N,N'-dicyclohexyl carbodiimide (2 g, 0.0097 mole) with stirring. The reaction mixture was stirred for 2 hours at room temperature. It was filtered and the filtrate on evaporation under reduced pressure gave crude product, which was purified by column chromatography (EtOAc:n-hexane=20:80) to give the title product as a yellow solid (1.0 g, 51%)

m.p.: 117–118° C.

IR(KBr): 1721, 1635, 1590, 1537 $cm^{-1}$

PMR (200 MHz, $CDCl_3$) δ: 3.91–4.16 (4H,m), 4.63–4.66 (1H,d,J=6 Hz), 5.07–5.12 (1H,dd,J=4.5 Hz), 5.39–5.68 (2H, m), 7.61–8.36 (3H,m)

Mass: 353 ($M^+$), 194, 163, 127.

Oral Formulations

Orally they may be administered as solid dosage forms for example as pellets, granules, powder, sachet or as discreet units such as tablets or capsules, etc. Other orally administered pharmaceutical preparations include monophasic and biphasic liquid dosage forms either in ready to use form, or forms suitable for reconstitution such as mixtures, syrups, suspensions or emulsions. The preparations in addition may contain diluents, dispersing agents, buffers, stabilizers, solubilizers, surface active agents, preservatives, chelating agents and/or other pharmaceutical additives. Aqueous or non aqueous vehicles or their combination may be used and if desired may contain suitable sweeteners, flavouring agents or similar substances. In the case of a suspension or emulsion a suitable thickening agent, suspending agent or emulsifying agent may be present. Pharmaceutical preparations can have a slow, delayed or controlled release of active ingredients as is provided by a matrix or diffusion controlled system.

Parenteral Formulations

For parenteral administration, the compounds or their salts or suitable complexes may be presented in a sterile vehicle which may be an aqueous or non aqueous vehicle or a combination thereof. The examples of vehicles are, water, ethyl oleate, oils and derivatives of polyols, glycols and their derivatives. It may contain additives common in injectable preparations like stabilizers, solubilizers, pH modifiers, buffers, antioxidants, cosolvents, complexing agents, tonicity modifiers, etc. Some suitable additives are, for example tartrate, citrate, or similar buffers, alcohols, sodium chloride, dextrose and high molecular weight liquid polymers. Another alternative is sterile powder for reconstitution. The compound may be administered in the form of injection, intravenous infusion/drip, or suitable depot preparation.

When the present invention, its salts or a suitable complex is presented as a discrete unit dosage form like a tablet, it may contain in addition medically inert excipients as are used in art. Diluents such as starch, lactose dicalcium phosphate, lubricants or similar additives like talc, magnesium stearate, polymeric substances like methyl cellulose, hydroxy propyl cellulose, fatty acids and derivatives, sodium starch glycollate, etc. can also be used.

EXAMPLE 12

Preparation of Oral Dosage Form of the Benzofuroxan Derivatives Given in Table 1

The compounds described in Table 1 can be prepared in the form of tablets, containing the active ingredient in the range of 0.03 to 3 mg per tablet. A typical tablet has the following composition:

| Active ingredient | as given above |
|---|---|
| Starch | 27 mg |
| Lactose | 70 mg |
| Polyvinyl pyrolidone (k-30) | 1.0 mg |
| Talc | 1.5 mg |
| Magnesium stearate | 0.5 mg |

EXAMPLE 13

Preparation of Parenteral Dosage Form of Benzofuroxan Derivatives Given in Table 1

A preparation suitable for parenteral administration has the following composition:

| Active ingredient | 1 mg. |
|---|---|
| Poly ethylene glycol-400 | 0.5 ml |
| Isotonic saline solution q.s. | 1 ml |
| or water for injection | |

These examples are presented by way of illustration alone and in no way limit the scope of the invention.

I claim:

1. A benzofuroxan compound represented by formula (I);

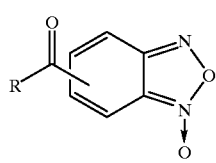

(I)

or pharmaceutically acceptable salts thereof wherein:

R is —O—$(CH_2)$n-X-R';

n=1 to 6;

X is —NHC(O)— or oxygen;

R' is lower alkyl ($C_1$–$C_8$), aromatic, heteroaromatic, substituted or unsubstituted saturated heterocyclic ring with one or two hetero atoms wherein substitution is with lower alkyl;

or R is selected from the group consisting of

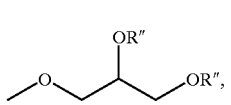

(a)

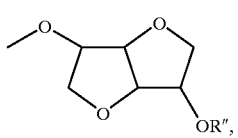

(b)

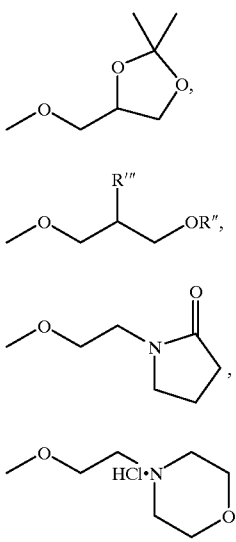

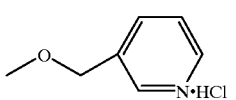

wherein R" is hydrogen, nitro, lower alkyl or —C(O)—R'" and
wherein R'" is hydrogen, lower alkyl or aryl.

2. The compound as claimed in claim 1, wherein the compound of formula (I) is substituted at the 5(6) position.

3. The compound as claimed in claim 1 or 2, wherein
X is —NHC(O)—;
R' is lower alkyl ($C_1$–$C_8$), heteroaromatic, substituted or unsubstituted saturated heterocyclic ring with one or two hetero atoms selected from the group consisting of nitrogen and oxygen wherein substitution is with lower alkyl and n is 1 or 2.

4. The compound as claimed in claim 1, wherein said compound is selected from the group consisting of:
   (a) 5(6)-(2-nicotinamide ethyloxycarbonyl) benzofuroxan hydrochloride,
   (b) 5(6)-(3-pyridine methoxy carbonyl) benzofuroxan,
   (c) 5(6)-((±)-2,2-dimethyl-1,3-dioxalane-4-methyloxycarbonyl) benzofuroxan,
   (d) 5(6)-(2-pyrolidinone ethyloxy carbonyl) benzofuroxan,
   (e) 5(6)-(2-isonicotinamide ethyloxy carbonyl) benzofuroxan hydrochloride,
   (f) 5(6)-(2-ethoxy ethyloxy carbonyl) benzofuroxan,
   (g) 5(6)-(2-hydroxy propyloxy carbonyl) benzofuroxan,
   (h) 5(6)-(isosorbide mononitrateoxycarbonyl) benzofuroxan,
   (i) 5(6)-(2,3-dihydroxy propyloxy carbonyl) benzofuroxan,
   (j) 5(6)-(2-methyloxy ethyloxy carbonyl) benzofuroxan and
   (k) 5(6)-(2-morpholino ethyloxy carbonyl) benzofuroxan.

5. A process for the preparation of the benzofuroxan compound of formula (I) as defined in claim 1, which comprises:
   a) reacting carboxy benzofuroxan and an equimolar amount of an alcohol selected from the group consisting of N-(2-hydroxyethyl)-nicotinamide, N-(2-hydroxyethyl) isonicotinamide, N-(2-hydroxyethyl)-2-pyrolidinone, N-(2-hydroxyethyl)morpholine, propylene glycol, methylcellosolve, ethylcellosolve, pyridine-3-methanol, solketal and isosorbide-5-mononitrate, in methylene chloride;
   b) adding 4-dimethylamino pyridine and N, N'-dicyclohexyl carbodiimide under stirring and continuing the stirring for a period of 2 to 16 hours at room temperature to complete the reaction;
   c) filtering the reaction mixture when the filtrate on evaporation under reduced pressure gives the crude product; and
   d) purifying the product thus obtained by column chromatography.

6. A process for the preparation of the benzofuroxan compound of formula (I) as defined in claim 1, which comprises:
   a) reacting chloro carbonyl benzofuroxan and an alcohol selected from the group consisting of N-(2-hydroxyethyl)-nicotinamide, N-(2-hydroxyethyl) isonicotinamide, N-(2-hydroxyethyl)-2-pyrolidinone, N-(2-hydroxyethyl)morpholine, propylene glycol, methylcellosolve, ethylcellosolve, pyridine-3-methanol, solketal and isosobide-5-mononitrate, in tetrahydrofuran at room temperature;
   b) adding a base triethylamine or trimethylamine to the reaction mixture;
   c) refluxing the reaction mixture until the completion of the reaction;
   d) removing the solvent, adding water and extracting with an organic solvent selected from the group consisting of dichloromethane, chloroform and ethyl acetate to form a solvent layer containing product and a water layer;
   e) removing organic solvent from the solvent layer obtained in step (d); and
   f) purifying by column chromatography.

7. A process for the preparation of the benzofuroxan compound of formula (I) as defined in claim 1, which comprises:
   reacting carboxybenzofuroxan with a solution of a corresponding alcoholic HCl, wherein said alcohol is selected from the group consisting of propylene glycol, methycellosolve and ethylcellosolve.

8. A process for the preparation of 5(6)-benzofuroxan of formula (I) as defined in claim 1, which comprises:
   cleaving a ketal, 5(6)-((±)-2,2-dimethyl-1,3-dioxolane-4-methyloxy carbonyl) benzofuroxan in a solvent under a mild acidic condition.

9. The process as claimed in claims 5, 6, 7 or 8, which comprises adding an acid to the compound so obtained to prepare a pharmaceutically acceptable salt thereof.

10. A method for treatment of cardiovascular disorders in mammals, which comprises administering an effective amount of the compound of formula (I) as claimed in claim 1 to a mammal in need of such treatment.

11. The method as claimed in claim 10, wherein said compound is used as a tolerance resistant anti-anginal compound.

12. The method as claimed in claim 10 or 11, wherein said compound is selected from the group consisting of
   (a) 5(6)-(2-nicotinamide ethyloxycarbonyl) benzofuroxan hydrochloride, (b) 5(6)-(3-pyridine methoxy carbonyl)-benzofuroxan, (c) 5(6)-((±)-2,2-dimethyl-1,3-dioxalane-4-methyloxycarbonyl) benzofuroxan, (d) 5(6)-(2-pyrolidinone ethyloxy carbonyl) benzofuroxan, (e) 5(6)-(2-isonicotinamide ethyloxy carbonyl) benzofuroxan hydrochloride, (f) 5(6)-(2-ethoxy ethyloxy carbonyl)benzofuroxan, (g) 5(6)-(2-hydroxy propyloxy carbonyl)benzofuroxan, (h) 5(6)-(isosorbide mononitrateoxycarbonyl) benzofuroxan, (i) 5(6)-(2,3-dihydroxy propyloxy carbonyl) benzofuroxan and (j) 5(6)-(2-methyloxy ethyloxy carbonyl)benzofuroxan.

13. A pharmaceutical composition containing a pharmaceutically active amount of the compound of formula (I) as claimed in claim 1 and a pharmaceutically acceptable carrier.

14. The pharmaceutical composition as claimed in claim 13 in the form of an oral formulation.

15. The pharmaceutical composition as claimed in claim 14, wherein said pharmaceutically acceptable carrier is selected from the group consisting of starch, lactose, polyvinyl pyrolidone (k-30), talc and magnesium stearate.

16. The pharmaceutical composition as claimed in claim 13 in the form of a parenteral formulation.

17. A process for the preparation of a parenteral formulation as claimed in claim 16, which comprises dissolving the active ingredient of general formula (I) in polyethylene glycol 400 and diluting the solution so obtained, with an isotonic solution or water to a desired concentration.

18. A method for the treatment of coronary heart disease in mammals, which comprises administering an effective amount of the compound of formula as defined in claim 1 to a mammal in need of such treatment.

19. The processes as claimed in claim 6, which comprises removing organic solvent from the solvent layer obtained in step (d) under reduced pressure.

* * * * *

UNITED STATES PATENT AND TRADEMARK OFFICE
CERTIFICATE OF CORRECTION

PATENT NO.    : 6,248,895 B1                                            Page 1 of 1
DATED         : June 19, 2001
INVENTOR(S)   : Sankaranarayanan, Alangudi It is certified that error appears in the above-identified patent and that said Letters Patent is hereby corrected as shown below:

Title page
ABSTRACT, replace

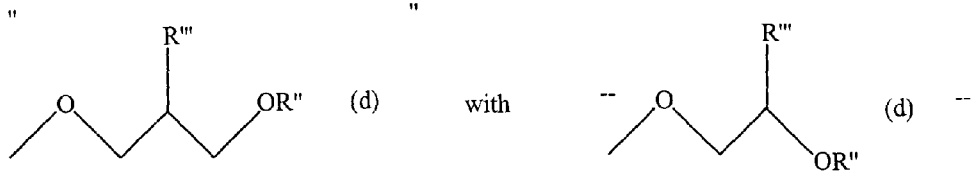

Column 4,
Lines 15-20, replace

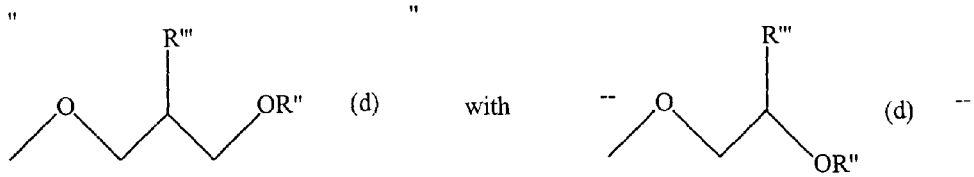

Column 15,
Lines 8-12, replace

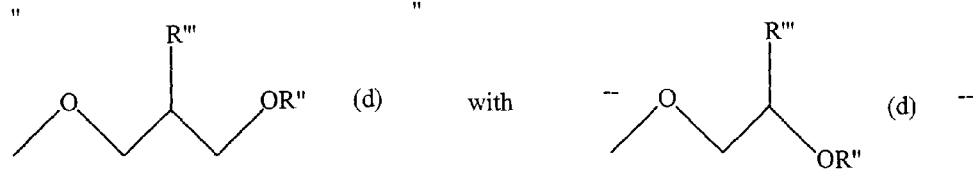

Signed and Sealed this

Twenty-fifth Day of February, 2003

JAMES E. ROGAN
*Director of the United States Patent and Trademark Office*